US010480936B2

(12) United States Patent
'T Hooft

(10) Patent No.: US 10,480,936 B2
(45) Date of Patent: Nov. 19, 2019

(54) OPTICAL SHAPE SENSING SYSTEM AND METHOD FOR SENSING A POSITION AND/OR SHAPE OF A MEDICAL DEVICE USING BACKSCATTER REFLECTOMETRY

(71) Applicant: KONINKLIJKE PHILIPS N.V., Eindhoven (NL)

(72) Inventor: Gert Wim 'T Hooft, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 32 days.

(21) Appl. No.: 15/574,533

(22) PCT Filed: Jun. 8, 2016

(86) PCT No.: PCT/EP2016/062928
§ 371 (c)(1),
(2) Date: Nov. 16, 2017

(87) PCT Pub. No.: WO2016/202649
PCT Pub. Date: Dec. 22, 2016

(65) Prior Publication Data
US 2018/0128600 A1  May 10, 2018

(30) Foreign Application Priority Data
Jun. 15, 2015  (EP) .................... 15172017

(51) Int. Cl.
*G01B 11/16* (2006.01)
*A61B 1/00* (2006.01)
(Continued)

(52) U.S. Cl.
CPC ........ *G01B 11/161* (2013.01); *A61B 1/00147* (2013.01); *A61B 1/00163* (2013.01);
(Continued)

(58) Field of Classification Search
CPC .................. G01B 11/18; G01B 11/2441; G01B 9/02027; G01B 9/0209; G01D 5/35306;
(Continued)

(56) References Cited

U.S. PATENT DOCUMENTS 5,798,521 A   8/1998  Froggatt
6,470,205 B2 * 10/2002  Bosselmann .......... A61B 34/70
                                                          600/424
(Continued)

OTHER PUBLICATIONS

Fercher, A.F. et al., "Measurement of intraocular distances by backscattering spectral interferometry", Optics Communications 117 (1995) 43-48.

*Primary Examiner* — Michael A Lyons

(57) ABSTRACT

Optical shape sensing system using backscatter reflectometry, comprising a broadband light source, an interferometer arrangement comprising a plurality of interferometers configured to perform backscatter reflectometry separately with a corresponding one of a plurality of input light beams divided from the input light and including a multi-core optical fiber, and a detector unit for detecting an output light beam, each interferometer comprising a fiber splitter dividing the corresponding input light beam into a reference beam and a device beam, an additional optical fiber for guiding the reference beam, a corresponding fiber core of the multi-core optical fiber guiding the device beam to be reflected within the medical device and guiding the reflected device beam, and a fiber coupler for coupling the reflected device beam with the reference beam forming the output light beam.

15 Claims, 3 Drawing Sheets

(51) Int. Cl.
  *A61B 5/06*   (2006.01)
  *A61M 25/01*  (2006.01)
  *G01B 9/02*   (2006.01)
  *G01B 11/24*  (2006.01)
  *A61B 34/20*  (2016.01)

(52) U.S. Cl.
  CPC .............. *A61B 5/065* (2013.01); *A61B 34/20* (2016.02); *A61M 25/01* (2013.01); *G01B 9/02004* (2013.01); *G01B 9/02027* (2013.01); *G01B 11/18* (2013.01); *G01B 11/2441* (2013.01); *A61B 2034/2061* (2016.02)

(58) Field of Classification Search
  CPC ........... G01D 5/35316; G01D 5/35329; G01D 5/35358; G01D 5/35361; G02B 6/02042; A61B 1/00165; A61B 2034/2061; A61B 34/20
  See application file for complete search history.

(56) References Cited

U.S. PATENT DOCUMENTS

| | | | |
|---|---|---|---|
| 6,545,760 | B1 | 4/2003 | Froggatt et al. |
| 7,772,541 | B2 | 8/2010 | Froggatt et al. |
| 7,781,724 | B2 | 8/2010 | Childers et al. |
| 8,773,650 | B2 | 7/2014 | Froggatt et al. |
| 8,909,040 | B1 | 12/2014 | Parker et al. |
| 2004/0104349 | A1* | 6/2004 | Chugg .................. G01T 7/00 250/370.01 |
| 2006/0013523 | A1 | 1/2006 | Childers et al. |
| 2009/0324161 | A1* | 12/2009 | Prisco .................. G01L 1/246 385/13 |
| 2011/0109898 | A1* | 5/2011 | Froggatt ................ G01B 11/18 356/73.1 |
| 2011/0119023 | A1* | 5/2011 | Duindam ............... G01B 21/22 702/150 |
| 2011/0202069 | A1* | 8/2011 | Prisco ................ G01D 5/35316 606/130 |
| 2012/0099112 | A1* | 4/2012 | Alphonse ........... G01B 9/02044 356/479 |
| 2017/0276523 | A1* | 9/2017 | Lally ................. G01D 5/35361 |
| 2017/0370704 | A1* | 12/2017 | Froggatt ................. G01L 1/242 |

\* cited by examiner

OPTICAL SHAPE SENSING SYSTEM AND METHOD FOR SENSING A POSITION AND/OR SHAPE OF A MEDICAL DEVICE USING BACKSCATTER REFLECTOMETRY

CROSS-REFERENCE TO PRIOR APPLICATIONS

This application is the U.S. National Phase application under 35 U.S.C. § 371 of International Application Serial No. PCT/EP2016/062928, filed on Jun. 8, 2016, which claims the benefit of European Patent Application No. 15172017.4, filed on Jun. 15, 2015. This application is hereby incorporated by reference herein.

FIELD OF THE INVENTION

The present invention relates to an optical shape sensing system and method for sensing a position and/or shape of a medical device using backscatter reflectometry. It finds application in minimal invasive intervention techniques, in particular in elongated medical devices such as fibers, endoscopes, catheters or guidewires.

BACKGROUND OF THE INVENTION

Optical shape sensing (OSS) is an optical measurement technique for determining the position and shape of a structure in a three-dimensional space. The Optical Shape Sensing (OSS) technology is also called Fiber-optical RealShape (FORS) technology. Optical Shape Sensing can be applied in minimal invasive procedures in healthcare, wherein it is advantageous to monitor the three-dimensional shape of an elongated medical device within the body of a patient.

To this end, the OSS is based on three techniques: first, strain sensing using spectroscopy; second, distributed sensing using interferometry; and third, shape reconstruction using a special fiber geometry. State of the art OSS techniques utilize strain sensing which entails the measurement of spectral shifts. In particular, a swept laser source is applied which generates light of a chosen wavelength, wherein the wavelength can be varied within a wavelength span. Such a swept laser source is also known as tunable laser source (TLS). A light beam generated by the TLS is split into a reference beam and a device beam by a fiber splitter. The device beam is directed towards a device under test (DUT) via a circulator. The device beam is reflected within the DUT and is redirected by the circulator to a fiber coupler. The reference beam is directly guided to the fiber coupler to form an output lighting combined from the reference beam and the reflected device beam. The output light beam can be monitored by a detector in order to retrieve interference signals resulting from constructive and destructive interferences between the reference beam and the reflected device beam.

Several requirements need to be fulfilled by the TLS utilized in the current implementations of OSS. Firstly, the spectral output of the laser needs to be monochromatic so that light travelling within the medical device, in particular being reflected between different inner surfaces along the fiber encapsulated by the medical device, will still have a well-defined phase in order to give rise to a proper interference with the light that only travels along the reference path of the interferometer. In other words, the coherence length of the laser should be much larger than twice the fiber length multiplied by the refractive index of the fiber. This means that the line width should be in the MHz range or lower. The line width is the width of the spectrum while the laser is not scanning. The smaller the spectral width the better the optical frequency (in MHz) and wavelength are determined, the longer is the coherence length (speed of light/frequency width).

Secondly, the sweeping of the laser over the entire spectral range should be linear in time. The latter requirement originates from the fact that the different fiber positions will only give rise to a specific beating frequency on the detector when the frequency range swept by the TLS is linear in time. Otherwise scrambling of optical data corresponding to adjacent fiber positions will occur. However, the TLS known in the art do not sufficiently fulfill this requirement. As a consequence, it is necessary to add an additional interferometer with a fixed delay length to the system. The signal from the additional interferometer is then used to linearize all other optical signals.

Thirdly, the scanning/sweeping speed of the laser should be sufficiently large. In optical shape sensing for medical applications, the fiber is incorporated in a catheter or guide wire. These devices are manipulated by hand and therefore prone to vibrations. Nevertheless, high stability, in particular interferometric i.e. sub-wavelength stability is required. Interferometric or sub-wavelength stability means that the path difference between the reference beam and the reflected device beams during the scan to precision should be significantly smaller than the wavelength, i.e. in the nanometer regime. This can only be achieved with a short acquisition time, requiring the laser to operate at a scanning speed of 10,000 nm/s or larger. Such a large scanning speed already gives rise to interferometric signals that are not purely linearly proportional to the delay length but also exhibit additional quadratic effects in delay.

U.S. Pat. No. 7,772,541 B2 discloses a fiber optic position and/or shape sensing device including an optical fiber with either two or more single core optical fibers or a multi-core optical fiber having two or more fiber cores. U.S. Pat. No. 7,781,724 B2 discloses a fiber optic position and shape sensing device comprising an optical fiber means, which comprises at least two single core optical fibers or a multi-core optical fiber having at least two fiber cores. These fiber optic position and shape sensing devices known in the art utilize swept laser sources to generate light for performing OSS.

SUMMARY OF THE INVENTION

It is an object of the present invention to provide an optical shape sensing system and method for sensing a position and/or shape of a medical device which enable optical shape sensing based on backscatter reflectometry while facilitating a proper interference between the reference beam and the device beam, avoiding data scrambling of adjacent fiber positions more easily as well as maintaining high stability of the system under vibrations.

In a first aspect of the present invention an optical shape sensing system for sensing a position and/or shape of a medical device using backscatter reflectometry is provided that comprises a broadband light source for generating input light of multiple wavelengths of a broadband spectrum, an interferometer arrangement comprising a plurality of interferometers including a multi-core optical fiber, the multi-core optical fiber comprising a plurality of fiber cores being a central core arranged in the center of the optical fiber and at least three outer cores helically wound around the central core, so that the outer cores are equidistant from each other in cross section perpendicular to a longitudinal direction of the optical fiber, wherein each of the interferometers is configured to perform backscatter reflectometry separately with a corresponding one of a plurality of input light beams divided from the input light and comprises a fiber splitter for dividing the corresponding input light beam into a reference beam and a device beam, an additional optical fiber for guiding the reference beam, a corresponding fiber core of the multi-core optical fiber for guiding the device beam to be reflected within the medical device and for guiding the reflected device beam, and a fiber coupler for coupling the reflected device beam with the reference beam to form an output light beam, the optical shape sensing system further comprising a spectrometer for receiving and interacting with the output light beam, the spectrometer comprising a detector unit for detecting the output light beam.

In a further aspect of the present invention a method for sensing a position and/or shape of a medical device using backscatter reflectometry is provided that comprises generating input light of multiple wavelengths of a broadband spectrum, performing backscatter reflectometry separately with a corresponding one of a plurality of input light beams divided from the input light using an interferometer arrangement comprising a plurality of interferometers including a multi-core optical fiber, the multi-core optical fiber comprising at least two fiber cores, wherein the backscatter reflectometry comprises dividing the corresponding input light beam into a reference beam and a device beam, using an additional optical fiber to guide the reference beam, using a corresponding fiber core of the multi-core optical fiber to guide the device beam to be reflected within the medical device and to guide the reflected device beam, and coupling the reflected device beam with the reference beam to form an output light beam, the method further comprising receiving and interacting with the output light beam and detecting the output light beam.

In yet further aspects of the present invention, there are provided a computer program which comprises program code means for causing a computer to perform the steps of the method disclosed herein when the computer program is carried out on the computer as well as non-transitory computer-readable recording medium that stores therein a computer product, which, when executed by a device, causes the method disclosed herein to be performed.

Preferred embodiments of the invention are defined in the dependent claims. It shall be understood that the claimed method and computer program have similar and/or identical preferred embodiments as the claimed system and as defined in the dependent claims.

The broadband light source has a sufficiently broad optical spectrum which preferably overlaps with the wavelength range, in which all typical wavelength shifts due to strain occur. The input light generated by the broad band light source is first divided into a plurality of input light beams. The interferometer arrangement is configured to perform backscatter reflectometry, wherein each individual interferometer is configured to perform interferometry with a corresponding individual input light beam separately.

For each interferometer, the input light beam is divided by the fiber splitter into two beams—the reference beam and the device beam. The reference beam is guided from the fiber splitter directly to the fiber coupler via a fiber section of the additional optical fiber, which is preferably a single-core optical fiber. The device beam is first guided into the medical device by the corresponding fiber core of the multi-core optical fiber and then reflected or backscattered within the medical device. The reflected device beam is subsequently guided to the circulator which redirects the reflected light beam to the fiber coupler. Hence, the path for guiding the reference beam between the fiber splitter and the fiber coupler is a reference branch, while the path for guiding the device beam between the fiber splitter and the fiber coupler is therefore a device branch.

Depending on the optical path length difference between the device beam and the reference beam and the wavelength of light, the reflected device beam and the reference beam give rise to constructive or destructive interference. In particular, constructive/destructive interference arises when the optical path length difference equals an even/odd amount of half of the wavelength.

The output light beam is received by the spectrometer, preferably by a grating of the spectrometer, with which the output light beam optically interacts. Subsequently, the output light beam is detected by the detector unit of the spectrometer. The spectrometer is configured to unravel the interference by separating the interference signals each corresponding to a different wavelength or wavelength interval. Alternatively, the output light beam may be received by one or more prisms, with which the output light beam interacts.

The optical shape sensing system is therefore an optical Fourier domain reflectometer (OFDR), which is able to obtain the strain and the curvature of the optical fiber inserted into the medical device or alternatively being itself the medical device, based on the reflectivity data. In this way, the optical Fourier domain reflectometer performs backscatter reflectometry or optical Fourier domain interferometry while using only reflectivity and interferometry measurements. The optical Fourier domain reflectometer may also be understood as a frequency domain reflectometer.

Advantageously, the afore-mentioned disadvantages associated with tunable laser sources (TLS) are overcome while high spectral resolution is facilitated so that the result of the optical shape sensing is highly reliable. Further, distributed scattering pattern, i.e. wavelength-dependent reflectivity and interferometry data obtained from the backscatter reflectometry, can be used to determine the spectral shift and the associated strain parameter of each segment of the fiber sensor by means of a computing device so that a position and/or shape can be evaluated for a portion of the fiber based on the strain parameters. The fiber sensor is the part of the multi-core optical fiber to be inserted into the interventional medical device introducible into a patient body. Alternatively, the multi-core optical fiber and/or the fiber sensor is itself the interventional medical device.

Using an interferometer "down-mixes" optical frequencies to much lower frequencies which are dispersed in space by the spectrometer. By a frequency analysis (Fourier transform) the signal as a function of optical frequency is transferred into a signal as a function of delay time, i.e. travel time along the fiber. The interferometer is therefore possible to gain distributed information, i.e. as a function of position on the fiber sensor.

Each core of the multi-core optical fiber is attached to a separate interferometer with a fiber splitter, a reference branch, a device branch and a fiber coupler, wherein the device branch preferably passes a circulator. A circulator is a three-port-device. A first port (port 1) is the input connected to the fiber splitter. A second port (port 2) is connected to a core of the multi-core fiber (DUT). A third port (port 3) is the output port connected to the coupler. The circulator connects port 1 to port 2, port 2 to port 3. The input light from the broadband light source is preferably split into the same number of input light beams as the number of cores of the multi-core optical fiber, the number being preferably four.

The various circulators in all the device branches have preferably an output port connected to a so-called "fan-out". The fan out is an optical element between the various circulators and the one multi-core fiber and couples a plurality of single-core fibers to a single fiber with multiple cores which is preferably attached to a multi-core device under test. Each core of the multi-core fiber extends preferably to the same length as the multi-core optical fiber. The central core and each of the three outer cores of the multi-core fiber carries a corresponding one of the light beams separately and independently from each other. Due to the equidistant arrangement of the outer cores leading to a regular shape, preferably a regular triangle geometry in the cross section, the strains introduced by bending of the entire fiber in the three outer cores cancel each other, so that the sum of their bending strains is essentially equal to zero. The number of the outer cores may be larger than three, wherein the outer cores may generally be arranged equidistantly in cross section.

Since the backscatter reflectometry is performed separately with each corresponding input light beam, the distributed scattering pattern can be obtained over the fiber sensor for each core and also the spectral shift. Consequently, the associated strain parameter of each segment of the fiber can be determined from each core separately without cross-talk between signals of different cores. When using four cores, four different strain signals are available over the length of the sensor. By proper combination of these strain signals one can evaluate the following four quantities as function of position along the fiber sensor: axial strain (or temperature), twist and curvature in two perpendicular directions orthogonal to the longitudinal axis of the fiber sensor. From these four quantities the exact shape in 3-dimensional space can be inferred.

In a preferable embodiment, the broad band light source comprises a super-luminescent light emitting diode. In this way, the input light beam can be generated while combining the advantages of high power and brightness with that of low coherence, leading to a highly effective broadband light source.

In another preferable embodiment, the broadband spectrum comprises a continuous optical band having a bandwidth of at least 20 nm. In this way, light of a large number of different wavelengths can be applied for carrying out optical shape sensing. Advantageously, the spectral bandwidth corresponds to a spatial resolution as low as 40 microns. The total spectral width determines the spatial resolution and the maximum amount of wavelength shift, i.e. the maximum amount of strain. The spectral resolution of the spectrometer determines the minimum amount of spectral shift and consequently the minimum amount of strain. It also determines the maximum allowable length of the sensor.

In another preferable embodiment, the continuous optical band comprises a central wavelength of essentially 1515 nm or 800 nm. In this way, besides the C band used for telecommunications, also an optical band around 800 nm can be used to perform OSS with increased sensitivity.

In another preferable embodiment, the grating comprises a plurality of scattering elements. This is advantageous for enabling distributed scatter pattern.

In another preferable embodiment, the detector unit comprises a detector array consisting of a plurality of detector elements arranged in an array. In this way, a pixelated detector unit is realized so that the detector unit is able to provide signal with high sensitivity.

Preferably, the grating is configured to distribute the output light beam into a plurality of beam components each consisting of light of a wavelength interval and propagating to a corresponding one of the detector elements of the detector array. In this way, the output light beam is separated into different beam components with light from a corresponding wavelength interval. Each beam component is detected by a corresponding detector element of the detector array. Therefore, the grating disperses the output light beam in various beam components depending on the wavelength. Advantageously, the different beam components are detected by different detector elements of the detector array, leading to high resolution of the spectrometer.

In another preferable embodiment, the detector array comprises at least 20000 detector elements in one dimension. In this way, the detector unit is highly pixelated leading to high detector resolution.

In another preferable embodiment, the detector array is a two-dimensional detector array. Advantageously, the detector array is able to detect the output light beam emanating from the grating in two dimensions, leading to increased detectable signal amount and thus higher reliability of the optical shape sensing. Preferably, one dimension of the two-dimensional array is used for dispersion of the broadband spectrum. Further preferably, the other dimension of the two-dimensional array is used for distributing different output light signals each originating from one of the cores of the multi-core optical fiber.

In another preferable embodiment, the detector unit is provided with an integration time between 1 millisecond (ms) and 2 ms. In this way, the sensitivity of the detector unit to vibrations due to handling of the medical device, particular the fiber sensor, can be reduced or even diminished.

In another preferable embodiment, the interferometer arrangement comprises a Mach-Zehnder interferometer comprising a circulator for directing the device beam to the multi-core optical fiber and to redirect the reflected device beam from the multicore optical fiber to the fiber coupler. The Mach-Zehnder interferometer is known to be widely applicable and highly precise for interferometric measurements. Advantageously, the present optical shape sensing system can be built with high precision. Alternatively, the interferometer arrangement may comprise a Michelson interferometer.

In another preferable embodiment, the optical shape sensing system further comprises a polarization controller for polarizing each input light beam into two input polarization states, the polarization controller being arranged between the broadband light source and the optical Fourier domain reflectometer. This embodiment facilitates a polarization diversity scheme enabling a measurement of birefringence. Advantageously, the result of optical shape sensing can be corrected by the contribution of birefringence, thus even more reliable.

Preferably, the optical shape sensing system further comprises a polarizing beamsplitter for splitting the output light beam into two signal portions each in a corresponding one of two output polarization states, the detector unit being configured to detect the two signal portions, the polarizing beamsplitter being arranged between the optical Fourier domain reflectometer and the detector unit. Advantageously, the birefringence can be determined precisely, enabling a more reliable correction of the OSS result.

Preferred embodiments of the invention are defined in the dependent claims. It shall be understood that the claim method has similar and/or identical preferred embodiments as the claimed device and as defined in the dependent claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Optical shape sensing (OSS) may be performed using three techniques: first, strain sensing using spectroscopy; second, distributed sensing using interferometry; and third, shape reconstruction using a special fiber geometry. State of the art techniques in OSS are based on strain sensing which entails the measurement of spectral shifts. Here, the typical measurement sensitivity is about 1.2 pm/με, wherein one με corresponds to a relative length increase of $10^{-6}$. In this way, the typical measurement sensitivity is determined by the minimal detectable wavelength shift.

Interferometry enables distributed sensing with a high spatial resolution. For instance, methods known in the past use a swept laser source or tunable laser source (TLS) so that the various strain sensors measured based on Bragg gratings can be distinguished from one another even when their spectral response is the same.

Each position within the fiber sensor is characterized by its own beat frequency which is proportional to the optical length difference between the device branch and the reference branch, and to the scan speed of the TLS. This means that a vast amount of sensing positions being the reflection positions become available even when the distance between the positions is small. The number of sensing positions lies typically in the range of $10^5$ or higher and is only determined by data acquisition. The total length of the optical fiber that can be interrogated, i.e. in which backscatter reflectometry can be performed, is given by $$L = \frac{\lambda^2}{4n\delta\lambda} \quad (1)$$

Here, $\lambda$ is the central wavelength, n is the refractive index of the light in the optical fiber and $\delta\lambda$ is the wavelength resolution, i.e. the wavelength increment or step between consecutive data points. For a few meters of length, the wavelength step should be as small as 0.1 pm for a central wavelength in the telecom regime (C band), i.e. from 1,525 to 1,565 nm. The total wavelength span $\Delta\lambda$ of the TLS determines the spatial resolution, i.e. the spatial increment between two consecutive sensor positions within the fiber:

$$\Delta z = \frac{\lambda^2}{2n\Delta\lambda} \quad (2)$$

Given the fact the strain due to bending can amount a few millistrains, the wavelength span should cover about 20 nm in order to achieve a proper spatial resolution. The ratio $\Delta\lambda/2\delta\lambda$ gives the amount of sensor points and, taking into account the afore-mentioned values of wavelength step and wavelength span, this ratio essentially equals $10^5$.

Figure 1:
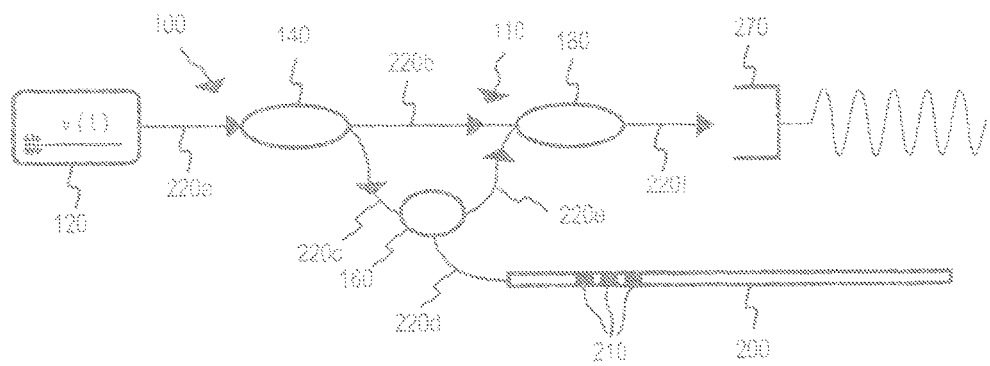
FIG. 1 shows schematically an optical shape sensing system comprising a tunable laser source.

FIG. 1 shows schematically an optical shape sensing system 100 comprising a Mach-Zehnder interferometer 110 connected to a tunable laser source (TLS) 120 and a detector unit 270. The Mach-Zehnder interferometer 110 comprises a fiber splitter 140 for dividing an input light beam generated by the TLS 120 and subsequently guided by a first fiber section 220a into a reference beam guided by a second fiber section 220b and a device beam guided by a third fiber section 220c.

The Mach-Zehnder interferometer 110 further comprises a circulator 160 for directing the device beam into a medical device 200 via a fourth fiber section 220d, wherein the fourth fiber section 220d is at least partially encapsulated in the medical device 200. The device beam is reflected within the medical device 200 at a certain reflection position 210. In particular, the fiber sensor comprises a Rayleigh scatter and/or a fiber Bragg grating, which interacts with the device beam, so that at least a portion of the incoming device beam is backscattered/reflected. The reflected device beam is guided back to the circulator 160 via the fourth fiber section 220d. The circulator 160 subsequently redirects the reflected device beam via a fifth fiber section 220e to be coupled with the reference beam by a fiber coupler 180 of the Mach-Zehnder interferometer 110. The fiber splitter 140 may divide the input light beam equally into the reference beam and a device beam, wherein the fiber coupler 180 may couple the reference beam and the reflected device beam which have equal signal amount. The fiber coupler 180 couples the reflected device beam with the reference beam to form an output light beam which is guided by a sixth fiber section 220f to be detected by the detector unit 270.

The optical path through the second fiber section 220b forms the reference branch of the Mach-Zehnder interferometer 110 and the optical paths through the third, the fourth and the fifth fiber sections 220c, d, e as well as the circulator 160 form the device branch of the Mach-Zehnder interferometer 110. The reflected device beam can interfere with the reference beam at the fiber coupler 180 leading to interference signals illustratively shown as wave in FIG. 1. The light path of the device branch, i.e. from the fiber splitter 140 via the reflection position 210 towards the fiber coupler 180, will be different in length from the light path of the reference branch. Consequently, at any moment in time the light in fiber section 220e towards the detector has two components which originate out of the tunable light source 120 from two different moments in time with a constant time difference. Since the optical frequency of the light source 120 is tuned linearly in time, a constant time difference gives rise to a constant optical frequency difference. The interference signals can be detected by the detector unit 270, wherein the beat frequency is proportional to the length difference between the device branch and the reference branch as well as to the scan rate of the TLS 120. The medical device 200 is also known as device under test (DUT).

In FIG. 1, only one grating within the fiber sensor at a particular position 210 is shown so that the detector unit 270 only measures one beat frequency. At position 210 a Bragg grating is written with a certain periodicity $\wedge$, this means that there is resonant wavelength $\lambda_B = n\wedge$, where the reflectivity is high in comparison to other wavelengths. The beat frequency corresponding to position 210 will only be recorded by detector 270 when the laser source 120 is tuned over this resonance. Strain will cause a change in the periodicity of the grating and consequently also give rise to a shift in the resonant wavelength. The detector unit 270 may also detect multiple beat frequencies each associated with its own optical spectrum containing the resonance wavelength of the corresponding grating.

Figure 2:
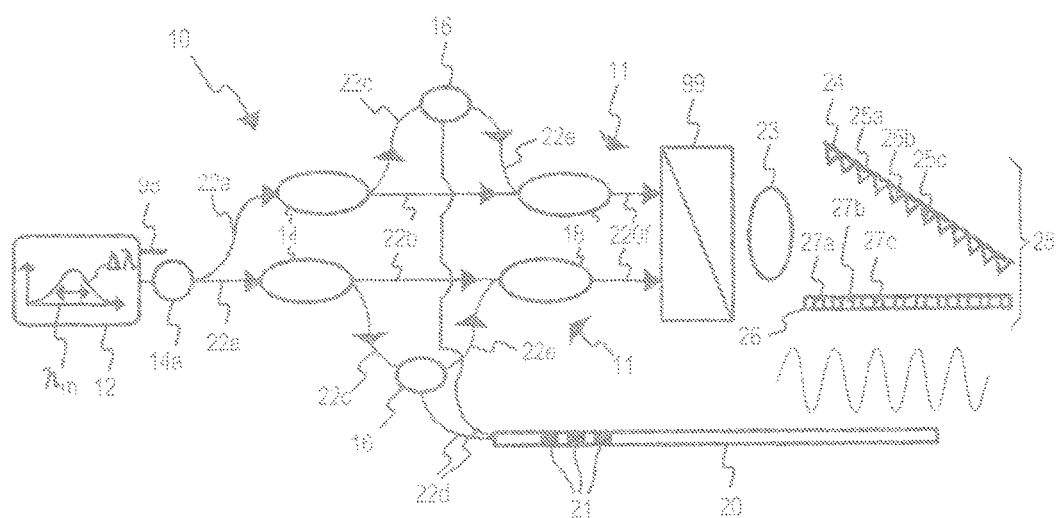
FIG. 2 shows schematically an optical shape sensing system comprising a broadband light source.

FIG. 2 shows schematically an optical shape sensing system 10 for sensing a position and/or shape of a medical device 20 (DUT) using backscatter reflectometry. The optical shape sensing system 10 comprises an interferometer arrangement 11 comprising a plurality of individual Mach-Zehnder interferometers (not separately shown in FIG. 2). Each Mach-Zehnder interferometer is optically connected to a broadband light source 12 and a spectrometer 28. Further, each Mach-Zehnder interferometer is connected between the same broadband light source 12 and the same spectrometer 28. The optical shape sensing system 10 comprises the broadband light source 12 and the spectrometer 28. The broadband light source 12 and the spectrometer 28 form in combination with the interferometer arrangement 11 an optical Fourier domain reflectometer (OFDR) for performing backscatter reflectometry.

Each individual Mach-Zehnder interferometer comprises a fiber splitter 14, a circulator 16, a fiber coupler 18 and a single-core optical fiber 22s comprising a plurality of single-core fiber sections 22a, 22b, 22c, 22d, 22e. Each Mach-Zehnder interferometer includes further a fiber core of a multi-core optical fiber 22m (shown in FIGS. 3-4 in more detail), which comprises a plurality of fiber cores, in particular four or more cores. In FIG. 2, only one single Mach-Zehnder interferometer is schematically shown.

It is understood that the fiber splitter 14, the circulator 16, the fiber coupler 18 and the single-core optical fiber 22a-e are provided in the same number of sets as the fiber cores of the multi-core optical fiber 22m. In this way, an arrangement is built, in which backscattering reflectometry can be performed using each individual fiber core of the multi-core fiber 22m in conjunction with a corresponding set of components separately.

Preferably, an additional fiber splitter 14a is provided to divide the broadband light generated by the broadband light source 12 into a plurality of input light beams each guided by a separate fiber section 22a. Further preferably, an additional fiber coupler is provided to couple each individual circulator 16 with the multi-core optical fiber 22m. Each individual input light beam is therefore guided separately from other input light beams to perform interferometry.

The sensing method used by the optical shape sensing system 10 is illustratively depicted by the schematic block diagram shown in FIG. 5 and will be explained in the following.

Figure 5:
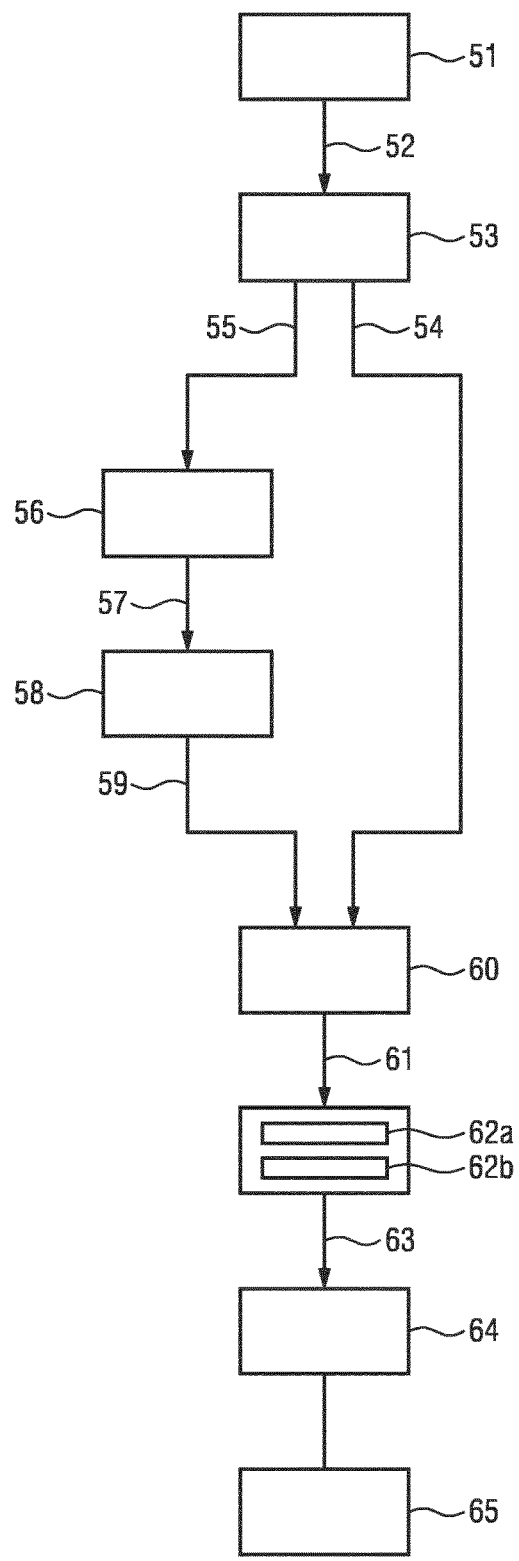
FIG. 5 shows a schematic block diagram of method for sensing the position and/or shape of a medical device.

The broadband light source 12 is configured to generate input light of multiple wavelengths (step 51 in FIG. 5). It comprises preferably a super-luminescent light emitting diode (LED) configured to generate light from a continuous optical band having a bandwidth of at least 20 nm. Further preferably, the central wavelength of the continuous optical band is essentially 1,550 nm or 800 nm. As shown illustratively by the diagram in conjunction with the broadband light source 12 in FIG. 2, the bandwidth is represented by $\Delta\lambda$ being the Full Width at Half Maximum (FWHM) of the intensity distribution of the generated light as a function of wavelength. The central wavelength is represented by $\lambda_m$. It is noted that the diagram shown in FIG. 2 is an illustrative representation of the intensity distribution of the generated light over the wavelength and does not claim to strictly reflect the intensity distribution in reality.

In a preferable embodiment, the bandwidth is about 20 nm with the central wavelength being around 1550 nm. This enables to measure strain values up to 8 millistrains which corresponds to a minimum radius of curvature of about 5 mm. Furthermore, according to Eq. (2), this corresponds to a spatial resolution of 50 μm.

The bandwidth for achieving the same minimum radius of curvature scales with the central wavelength. In another preferable embodiment, the bandwidth is about 10 nm with the central wavelength being around 800 nm. Following Eq. (2), an embodiment with a central wavelength of around 800 nm and a spatial resolution of 50 μm may have a bandwidth of about 5 nm.

For each individual Mach-Zehnder interferometer, the input light beam generated by the broadband light source 12 is guided by the first fiber section 22a to the fiber splitter 14 (step 52 in FIG. 5), which is configured to divide the input light beam into a reference beam and a device beam (step 53 in FIG. 5). The reference beam is then guided by the second fiber section 22b directly to the fiber coupler 18 (step 54 in FIG. 5). The device beam is first guided to the circulator 16 by the third fiber section 22c (step 55 in FIG. 5). The circulator 16 is configured to direct the device beam towards a medical device 20 (step 56 in FIG. 5) such as a catheter, a guidewire or a coating.

For this purpose, the multi-core optical fiber 22m which is partially encapsulated in the medical device 20 or alternatively itself the medical device is configured to guide the directed device beam (step 57 in FIG. 5) before and after the device beam is backscattered within the medical device 20. The reflected device beam is guided back to the circulator 16, which subsequently redirects the reflected device beam (step 58 in FIG. 5) towards the fiber coupler 18 via the fourth fiber portion 22d (step 59 in FIG. 5). The portion of the multi-core fiber 22m encapsulated in the medical device 20 (DUT) forms the optical fiber sensor. Alternatively, the entire multi-core fiber 22m is the optical fiber sensor or DUT.

Still for each individual Mach-Zehnder interferometer, the fiber coupler 18 is configured to couple the reference beam and the reflected device beam to form an output light beam (step 60 in FIG. 5). The output light beam is further guided towards the spectrometer 28 via the fifth fiber portion 22e (step 61 in FIG. 5).

Figure 3:
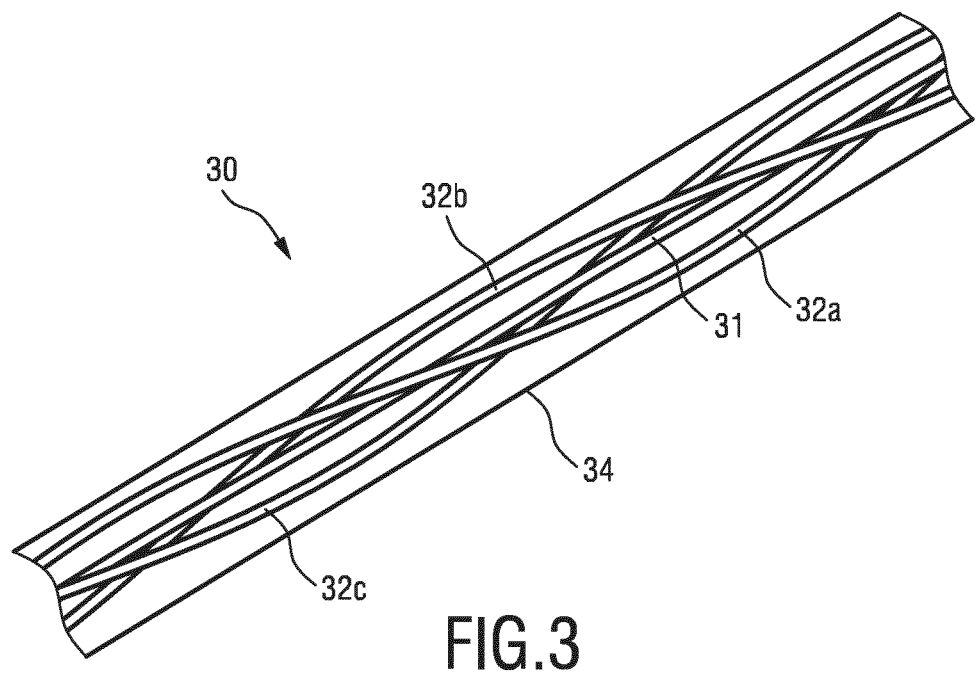
FIG. 3 shows schematically a multi-core optical fiber.

The fiber sensor incorporated in the medical device is a multi-core fiber with preferably 4 or more cores. An exemplary multi-core fiber sensor 30 is schematically shown in FIG. 3, which shows a central core 31 helically wound by three outer cores 32a,b,c. Each core 31, 32a,b,c is preferably embedded in a cladding. The cores 31, 32a,b,c are protected by a coating 34, preferably a polymer coating. The central core 31 is arranged in the center of the optical fiber sensor so that it extends along the longitudinal axis of the multi-core fiber sensor 30. The three outer cores 32a,b,c are equidistant from each other in a cross section (shown in FIG. 4) perpendicular to the longitudinal direction of the optical fiber sensor 30.

Figure 4:
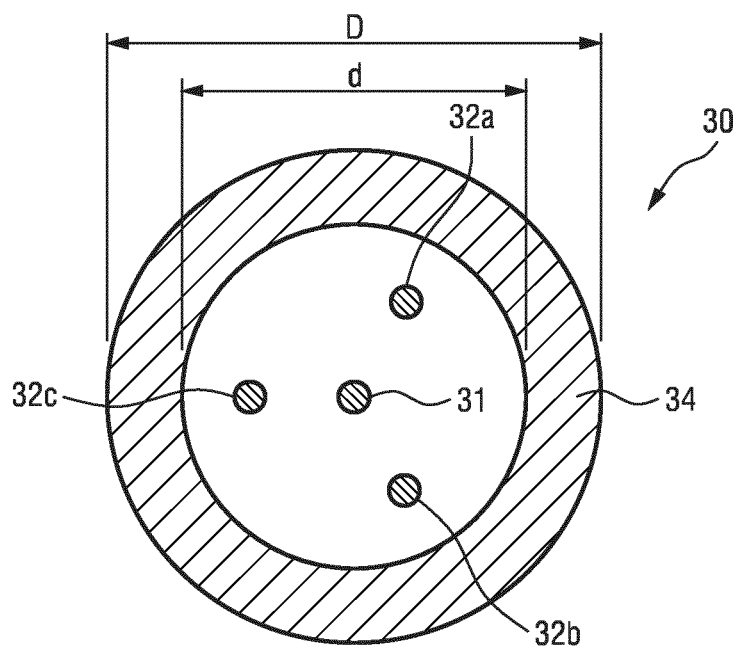
FIG. 4 shows schematically the multi-core optical fiber of FIG. 3 in cross section.

As can be seen in FIG. 4, the three outer cores 32a,b,c are arranged in the form of a regular triangle with the central core 31 being in the center of the regular triangle. The outer diameter D of the coating 34 may be 235 μm. The outer diameter d of the cladding may be 125 μm. The diameter of each core 31, 32a,b,c may be 7 μm. The distance between each outer core 32a,b,c and the central core 31 may be 35 μm.

For each of the cores 31, 32a,b,c an individual Mach-Zehnder interferometer is provided. To this end the light generated by the broadband light source 12 can be split into four input light beams and each of the circulators is attached to a corresponding lead wire of a fan out which couples a plurality of single core fibers to the multi-core fiber 22m.

The outputs of each of the interferometers can be guided to the spectrometer 28. The spectrometer 28 may have a 2D detector array so that one dimension of the array can be used for dispersion of the spectrum and the other dimension for distributing the various signals of the different cores 31, 32a,b,c of the medical device 20. Since each of the four cores of the multi-core fiber 22m is configured to guide a corresponding light beam, each Mach-Zehnder interferometer of the interferometer arrangement 11 is able to perform backscatter reflectometry and/or interferometry separately with each corresponding light beam.

The central core 31 is neutral to bending or torque, meaning that the central core is configured to monitor only axial strain which is mainly caused by temperature changes along the length of the fiber sensor 30. The axial strain signal is used for nulling the signals of the other three cores 32a,b,c in a so-called common mode rejection.

The three outer cores 32a,b,c of the fiber sensor 30 are helically wound around the central core 31 with a particular pitch or twist rate, i.e. turns per meter. When the fiber sensor which is encapsulated within the medical device 20 is torqued, the twist rate of the three outer cores will change correspondingly giving rise to a simultaneous length change i.e. strain. A bending force on the other hand will change the strain of the three outer cores 32a,b,c differently. In particular, when taking the same axial position for all three outer cores 32a,b,c into account, the bent part of the fiber comprises an outer side and an inner side, wherein the outer side has a larger opening angle compared to the inner side of the bent part of the fiber sensor 30. Since the three outer cores 32a,b,c are helically wound around the central core 31, the three outer cores 32a,b,c are either closer to the inner side or the outer side within the bent part of the fiber sensor 30. Depending on whether a specific outer core is closer to the inner side or the outer side, the specific outer core is bent essentially along the inner side or the outer side of the bent fiber part. Due to the regular triangle geometry of the three outer cores 32a,b,c in a cross section perpendicular to the longitudinal direction of the optical fiber sensor 30, the sum of the bending strains of the outer cores 32a,b,c will be essentially zero at each axial position along the fiber sensor 30.

Consequently, the average strain of the outer cores 32a,b,c is able to indicate the torque of the optical fiber sensor 30. In particular, from the difference of strain between the outer cores 32a,b,c it is able to evaluate the bending strain of the entire optical fiber sensor 30 in two directions orthogonal to each other. A curvature of the fiber sensor gives rise to a bending strain proportional to the ratio between the core-to-center distance on one hand, i.e. the distance between the outer core and the center of the fiber, and the radius of the curvature on the other hand. Therefore, when the radius of curvature in two orthogonal directions is known for each axial position of the fiber sensor 30, one can calculate the shape of the fiber by summing up the bending angles along the length of the fiber sensor 30, which is the part of the fourth fiber section 22d encapsulated within the medical device 20. Alternatively, the fourth fiber section 22d itself forms the medical device.

The reflected device beam gives rise to constructive/destructive interference after being coupled with the reference beam, dependent on the length difference between the reference path and the reference path, as well as on the wavelength. In particular, constructive/destructive interference arises when the path length difference equals an even/odd amount of half wavelength. The reference path and the device path are understood analogously to FIG. 1.

The spectrometer 28 comprises a grating 24 which preferably comprises a plurality of scattering elements 25a,b,c, wherein the grating 24 is configured to receive and interact with the output light beam (step 62a in FIG. 5). The grating 24 preferably makes from a parallel output light beam a diverging output light beam with a correspondence between angle of scattered light and wavelength. The division of the broadband spectrum into various wavelength-dependent spectral portions is done by the detector array and its pixels.

Further, the spectrometer 28 comprises a detector unit 26 for detecting an output light signal from the output light beam having interacted with the grating 24 (step 62b in FIG. 5). Preferably, the detector unit 26 comprises a detector array consisting of a plurality of detector elements 27a, b, c arranged in an array. The detector array may comprise at least 20000 detector elements 27a, b, c in one dimension, wherein each detector element 27a,b,c may correspond to a pixel. Also, the detector array may be a two-dimensional detector array. The spectrometer 28 monitors the output light beam, wherein the monitor signal is illustratively represented by the wave in FIG. 2. Preferably, a lens element 23 for collimating the output light beam from the fiber section 22e is arranged between the fiber coupler 18 and the spectrometer 28. The lens element 23 may be used to collimate a plurality of output light beams each originating from a different input light beam using a corresponding interferometer.

Further preferably, the grating 24 is configured to distribute the output light beam into a plurality of beam components each consisting of light of a wavelength interval and propagating under different spade angle, in particular in the direction of a corresponding one of the detector elements of the detector array. In this way, the output light beam is separated into different beam components, each containing light from a corresponding wavelength interval from the whole spectrum of the generated broadband light. Each beam component is detected by a corresponding detector element of the detector array. Therefore, the grating disperses the output light beam in various beam components depending on the wavelength. In FIG. 2, only one position 21 in the fiber sensor is shown, at which the device beam is scattered or reflected. The three stripes on the medical device 20 depict a theoretical Bragg grating with a periodicity. This periodicity may have a length of essentially 0.5 μm while the spatial resolution corresponding to a total spectral range of 20 nm equals essentially 50 μm. The spatial resolution limits the accuracy of determining the fiber position 21. The smallest possible wavelength interval is determined by the pixel size of the detector array, the distance between grating and the array as well as the dispersive power of the grating, i.e. limes/mm.

The interference pattern can thus be unraveled in the spectrometer. The spatial beat frequency on the detector array is proportional to the path length difference and therefore position within the device under test. Alternatively to a spectrometer, a single point detector may be applied in conjunction with a rotatable grating. In particular, the grating can be rotated in time so that a desired spectrum can be scanned completely.

The detected output light signal can be further guided to an analysis unit (step 63 in FIG. 5), in particular a computing device, which performs a frequency analysis to obtain strain data and/or curvature of the fiber sensor (step 64 in FIG. 5). In particular, the reflectivity data contain reflectivity being the power and/or intensity of the detected output light signal as a function of the wavelength. By applying a Fourier transformation, the reflectivity data are transformed so that reflectivity is represented as a function of the scattering position along the fiber sensor. The strain and/or curvature of the fiber sensor can thus be determined as a function of the axial position of the fiber sensor. From the strain and/or curvature data, the position and/or shape of the fiber sensor can be calculated (step 65 in FIG. 5).

The optical shape sensing system 10 shown in FIG. 2 is advantageous over systems known in the art firstly by comprising a broadband light source with a broad spectrum instead of a tunable light source with a static light source; secondly by comprising a spectrometer with a spectral resolution instead of a single point detector. For a pixelation of 20000 pixels over a length of 20 nm, the spatial resolution is essentially equal to 1 pm. In particular, the spectrum of the broadband light source 12 in FIG. 2 overlaps with the wavelength range, in which all typical wavelength shifts due to strain in the fiber sensor occur. Further, the system 10 shown in FIG. 2 is advantageous over the art by the fact that the spectral information is obtained by the system 10 shown in FIG. 2 as a function of the position parameter in the fiber sensor, instead of time.

The amount of positions within the fiber sensor that can be interrogated, i.e. where backscatter reflectometry can be performed, is again given by the ratio of Eqs. (1) and (2) shown above. In a straightforward implementation this would, taking the Nyquist theorem into account, result in half the amount of pixels on the detector array. Large detector arrays are therefore preferred. Detector arrays may have more than $2 \times 10^4$ pixels in one dimension. The width of spectrum limits either the amount of strain detectable, which corresponds to the smallest bending radius of the fiber sensor for optical shape sensing; or the spatial resolution of the fiber sensor whose reflectivity data can be obtained. The detection capability of the detector array can be improved by using a 2-dimensional array and folding the spectrum with a special design of the grating. In particular, a possibility is to disperse the spectrum using a grating. By a second dispersive element in the orthogonal direction one obtains a multitude of spectra distributed in two directions.

The optical shape sensing system 10 preferably comprises a polarization diversity scheme involving a polarization controller 98 for polarizing each input light beam into two input polarization states. The polarization controller may be arranged between the broadband light source and the interferometer arrangement 11. The polarization diversity scheme further involves a polarizing beam splitter 99 for splitting each output light beam into two signal portions each in a corresponding one of two output polarization states. For this purpose, the detector unit 26 may be configured to detect the two signal portions. Further the polarization beam splitter may be arranged between the interferometer arrangement 11 and the detector unit 26. Advantageously, the birefringence can be determined precisely by the polarization diversity scheme, enabling a more reliable correction of the OSS result. Preferably, the optical shape sensing system 10 comprises a single spectrometer with a two-dimensional detector array with a number of pixels in each dimension, where the number is a multiple of eight.

The integration time of the detector array may be limited to a range from 1 ms to 2 ms in order to avoid sensitivity to vibrations while handling the fiber sensor. Such an integration time is comparable to the scan time in an optical Fourier domain reflectometer using a swept laser source with a scanning rate of 10000 nm/s over a wavelength interval of 10 to 20 nm. On the other hand, in an optical shape sensing system such as that shown in FIG. 2 using a spectrometer, the power of the light generated by the broadband light source 12 is divided over many pixels of the detector array. This shows that, in case the power of the light generated by the two different light sources, TLS and broadband light source, in the two different optical shape sensing systems 10, 100 are the same and the measured spectrum is acquired for the same amount of data points, the signal to noise ratio (SNR) will also be the same for the two systems 10, 100.

Another advantage of an optical Fourier domain reflectometer using a spectrometer is that bright broadband light sources are available at other wavelength ranges than the telecom C-band. An optical Fourier domain reflectometer working at a central wavelength of essentially 800 nm has various advantages. Firstly, it is centered at the wavelength where detector arrays based on silicon technology have their highest sensitivity. These detector arrays are most cost effective and can be built with the largest amount of pixels. Secondly, the intensity of scattered light in Rayleigh scattering scales with the inverse of the wavelength to the power of four. Going from a wavelength around 1550 nm to 800 nm thus increases the intensity of the scattered light by a factor of 14. Thirdly, in an interferometer, all strain information including change in fiber length is determined as a function of wavelength. This means that the phase information in all signals has a sensitivity that is inversely proportional to the wavelength. Hence, by decreasing the wavelength from 1550 nm to 800 nm, the system will become almost twice as sensitive to strain, and thus to bending and twisting of the fiber sensor.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An optical shape sensing system for sensing a position and/or shape of a medical device using backscatter reflectometry, comprising:
   a broadband light source for generating input light of multiple wavelengths of a broadband spectrum,
   an interferometer arrangement comprising a plurality of interferometers including a multi-core optical fiber, the multi-core optical fiber comprising at least two fiber cores, wherein each of the interferometers is configured to perform backscatter reflectometry separately with a corresponding one of a plurality of input light beams divided from the input light and comprises:
- a fiber splitter for dividing the corresponding input light beam into a reference beam and a device beam,
- an additional optical fiber for guiding the reference beam,
- a corresponding fiber core of the multi-core optical fiber for guiding the device beam to be reflected within the medical device and for guiding the reflected device beam, and
- a fiber coupler for coupling the reflected device beam with the reference beam to form an output light beam, the optical shape sensing system further comprising
- a spectrometer for receiving and dispersing the output light beam from each interferometer, the spectrometer comprising a detector unit for detecting the output light beam from each interferometer.

2. Optical shape sensing system according to claim 1, wherein the broadband light source comprises a superluminescent light emitting diode.

3. Optical shape sensing system according to claim 1, wherein the broadband spectrum comprises a continuous optical band having a bandwidth of at least 20 nm centered at 1550 nm.

4. Optical shape sensing system according to claim 1, wherein the broadband spectrum comprises a continuous optical band having a bandwidth of at least 5 nm centered at 800 nm.

5. Optical shape sensing system according to claim 1, wherein the detector unit comprises a detector array consisting of a plurality of detector elements arranged in an array.

6. Optical shape sensing system according to claim 5, wherein the detector array comprises a two-dimensional array.

7. Optical shape sensing system according to claim 6, wherein one dimension of the two-dimensional array is used for dispersion of the broadband spectrum, wherein the other dimension of the two-dimensional array is used for distributing different output light signals each originating from one of the cores of the multi-core optical fiber.

8. Optical shape sensing system according to claim 1, wherein the multi-core optical fiber comprises a central core arranged in the center of the multi-core optical fiber and at least three outer cores helically wound around the central core.

9. Optical shape sensing system according to claim 8, wherein the outer cores are equidistant from each other in cross section perpendicular to a longitudinal direction of the optical fiber.

10. Optical shape sensing system according to claim 1, wherein the detector unit is provided with an integration time between 1 millisecond and 2 milliseconds.

11. Optical shape sensing system according to claim 1, wherein the interferometer arrangement comprises a Mach-Zehnder interferometer comprising a circulator for directing the device beam to the multi-core optical fiber and to redirect the reflected device beam from the multicore optical fiber to the fiber coupler.

12. Optical shape sensing system according to claim 1, further comprising a polarization controller for polarizing each input light beam into two input polarization states, the polarization controller being arranged between the broadband light source and the interferometer arrangement.

13. Optical shape sensing system according to claim 12, further comprising a polarizing beamsplitter for splitting the output light beam into two signal portions each in a corresponding one of two output polarization states, the detector unit being configured to detect the two signal portions, the polarizing beamsplitter being arranged between the interferometer arrangement and the detector unit.

14. A method for sensing a position and/or shape of a medical device using backscatter reflectometry, comprising:
- generating input light of multiple wavelengths of a broadband spectrum,
- performing backscatter reflectometry separately with a corresponding one of a plurality of input light beams divided from the input light using an interferometer arrangement comprising a plurality of interferometers including a multi-core optical fiber, the multi-core optical fiber comprising at least two fiber cores, wherein the backscatter reflectometry comprises:
  - dividing the corresponding input light beam into a reference beam and a device beam,
  - using an additional optical fiber to guide the reference beam,
  - using a corresponding fiber core of the multi-core optical fiber to guide the device beam to be reflected within the medical device and to guide the reflected device beam, and
  - coupling the reflected device beam with the reference beam to form an output light beam, the method further comprising
- receiving and dispersing the output light beam and detecting the output light beam from each of the plurality of interferometers in a spectrometer.

15. Non-transient computer program product having encoded thereon a computer program for sensing a position and/or shape of a medical device, the computer program comprising program code means for causing an optical shape sensing system carry out the steps of
- generating input light of multiple wavelengths of a broadband spectrum,
- performing backscatter reflectometry separately with a corresponding one of a plurality of input light beams divided from the input light using an interferometer arrangement comprising a plurality of interferometers including a multi-core optical fiber, the multi-core optical fiber comprising at least two fiber cores, wherein the backscatter reflectometry comprises:
  - dividing the corresponding input light beam into a reference beam and a device beam,
  - using an additional optical fiber to guide the reference beam,
  - using a corresponding fiber core of the multi-core optical fiber to guide the device beam to be reflected within the medical device and to guide the reflected device beam, and
  - coupling the reflected device beam with the reference beam to form an output light beam, and
- receiving and dispersing the output light beam and detecting the output light beam from each of the plurality of interferometers in a spectrometer.

* * * * *